United States Patent
Rochat et al.

(10) Patent No.: US 11,253,530 B2
(45) Date of Patent: *Feb. 22, 2022

(54) SYNERGISTIC PRODUCTION OF BUTYRATE ASSOCIATED WITH THE COMPLEXITY OF HMOS BLEND FOR USE IN INFANTS OR YOUNG CHILDREN FOR HEALTH PURPOSES

(71) Applicant: SOCIETE DES PRODUITS NESTLE S.A., Vevey (CH)

(72) Inventors: Florence Rochat, Montreux (CH); Laurent Favre, Carrouge (CH); Norbert Sprenger, Savigny (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/611,282

(22) PCT Filed: May 4, 2018

(86) PCT No.: PCT/EP2018/061527
§ 371 (c)(1),
(2) Date: Nov. 6, 2019

(87) PCT Pub. No.: WO2018/206434
PCT Pub. Date: Nov. 15, 2018

(65) Prior Publication Data
US 2020/0163981 A1    May 28, 2020

(30) Foreign Application Priority Data

May 9, 2017 (EP) .................................... 17170064

(51) Int. Cl.
*A61K 31/702* (2006.01)
*A61P 1/00* (2006.01)
*A61K 9/00* (2006.01)

(52) U.S. Cl.
CPC .......... *A61K 31/702* (2013.01); *A61K 9/0056* (2013.01); *A61K 9/0095* (2013.01); *A61P 1/00* (2018.01)

(58) Field of Classification Search
CPC .. A61K 31/702; A61K 9/0056; A61K 9/0095; A61K 9/0085
See application file for complete search history.

(56) References Cited

U.S. PATENT DOCUMENTS

| | | | |
|---|---|---|---|
| 10,609,945 B2 * | 4/2020 | Binia | A23L 33/105 |
| 2012/0171166 A1 | 7/2012 | Chow et al. | |
| 2013/0251844 A1 | 9/2013 | Sprenger et al. | |
| 2014/0335065 A1 * | 11/2014 | Davis | A23L 33/28 424/93.44 |
| 2016/0296541 A1 | 10/2016 | Sangild | |
| 2016/0296542 A1 | 10/2016 | Sangild | |

FOREIGN PATENT DOCUMENTS

WO     2016046294     3/2016

OTHER PUBLICATIONS

Kries (British Medical Journal, 1999, vol. 319, pp. 147-150.*
Lin et al. "Butyrate and Propionate Protect against Diet-Induced Obesity and Regulate Gut Hormones via Free Fatty Acid Receptor 3-Independent Mechanisms" PLoS ONE, Apr. 2012, vol. 7, issue 4, e35240, 9 pages.
Li et al. "Microbial Composition and In Vitro Fermentation Patterns of Human Milk Oligosaccharides and Prebiotics Differ between Formula-Fed and Sow-Reared Piglets" The Journal of Nutrition, 2012, vol. 142, pp. 683-689.
Stilling et al. "The neuropharmacology of butyrate: The bread and butter of the microbiota-gut-brain axis?" Neurochemistry International, 2016, vol. 99, pp. 110-132.
Nylund et al. "Severity of atopic disease inversely correlates with intestinal microbiota diversity and butyrate-producing bacteria" Allergy, 2015, vol. 70, pp. 241-244.
Makarova, "Prebiotics as "Functional" Component of Child Nutrition", Current Pediatrics, vol. 12, Issue No. 5,2013, pp. 8-15, English abstract considered.
Russia Patent Office Communication for Application No. 2019133073, dated Aug. 30, 2021, 20 pages.

* cited by examiner

*Primary Examiner* — Pancham Bakshi
(74) *Attorney, Agent, or Firm* — K&L Gates LLP (57) ABSTRACT

The present invention relates to a nutritional composition comprising at least three human milk oligosaccharides, for use to increase butyrate production in the digestive tract in an infant or a young child. The production increases with the HMOs blend complexity.

7 Claims, 2 Drawing Sheets

SYNERGISTIC PRODUCTION OF BUTYRATE ASSOCIATED WITH THE COMPLEXITY OF HMOS BLEND FOR USE IN INFANTS OR YOUNG CHILDREN FOR HEALTH PURPOSES

CROSS REFERENCE TO RELATED APPLICATIONS

The present application is a National Stage of International Application No. PCT/EP2018/061527, filed on May 4, 2018, which claims priority to European Patent Application No. 17170064.4, filed on May 9, 2017, the entire contents of which are being incorporated herein by reference

FIELD OF THE INVENTION

This invention relates to nutritional compositions comprising diverse human milk oligosaccharides especially for use in increasing butyrate production in the digestive tract in infants or young children. They may be used to prevent and/or treat a health disorder (inflammation, allergies, obesity, diabetes, infections . . . ) and/or promote a health benefit (gut benefits, anti-cancer effects . . . ) in said infants or young children.

BACKGROUND OF THE INVENTION

Mother's milk is recommended for all infants for various reasons. In comparison to formula feeding, breastfeeding has especially been reported to be beneficial for prevention against obesity (Owen et al, Effect of Infant Feeding on the Risk of Obesity Across the Life Course: A Quantitative Review of Published Evidence, 2005) or against infections (Quigley et al., Breastfeeding and Hospitalization for Diarrheal and Respiratory Infection in the United Kingdom Millennium Cohort Study, 2007; Hanson, Feeding and infant development Breast-feeding and immune function, 2007). Additionally, breast fed infant have a different gut microbiota profile as compared to infants fed with infant formula. Altogether, these factors affect the development of the infant physiology, including metabolism, immunity, protection against infections and overall growth. However, in some cases breastfeeding is inadequate or unsuccessful for medical reasons or the mother chooses not to breast feed. Infant formula have been developed for these situations. Fortifiers have also been developed to enrich mother's milk or infant formula with specific ingredients.

Prebiotics are non-digestible carbohydrates that contribute to the well-being of their host. They are typically compounds that pass undigested through the upper part of the gastrointestinal tract and stimulate the growth and/or activity of advantageous bacteria such as *bifidobacteria* that colonize the large bowel by acting as substrate for them or via a cross feeding.

Human milk oligosaccharides (HMOs) are, collectively, the third largest solid constituents in human milk, after lactose and fat. HMOs usually consist of lactose at the reducing end with a carbohydrate core that often contains a fucose or a sialic acid at the non-reducing end. There are over one hundred milk oligosaccharides that have been isolated and characterized in human milk.

Some compositions using HMO ingredients, such as fucosylated oligosaccharides, lacto-N-tetraose, lacto-N-neotetraose and/or sialylated oligosaccharides, have been described for different health purposes, mainly immune purposes.

Figure 4:
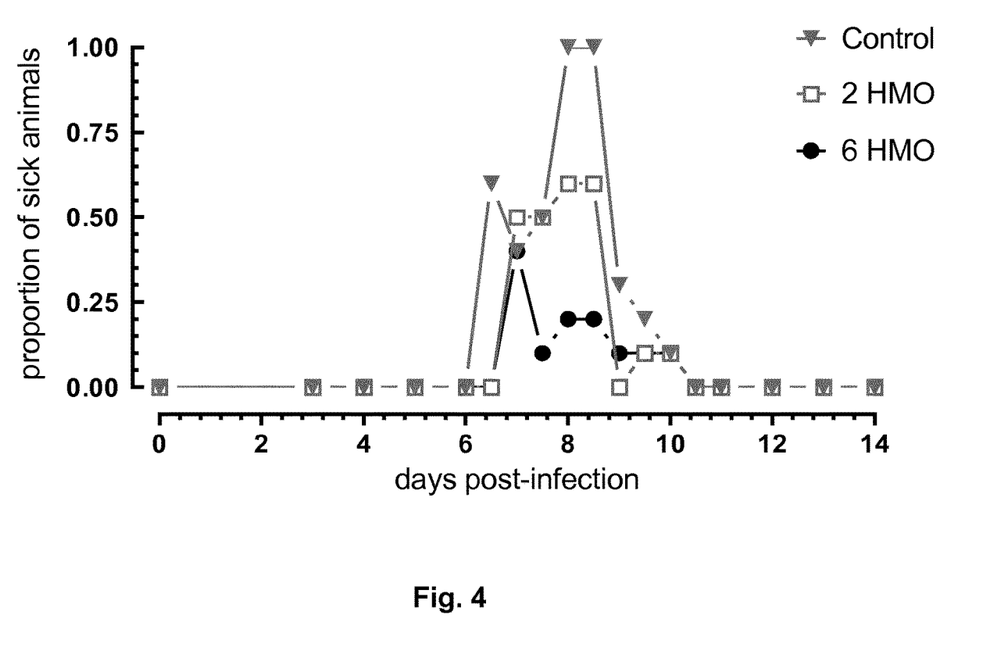
FIG. 4 represents the proportion of control, 2 HMO and 6 HMO treated animals showing sickness symptoms over time upon influenza virus infection on day. N=10 per group.

HMOs have been individually described as favorazing the production of SCFA like in WO12092155 (see FIG. 4 of this application). Short Chain fatty acids (SCFAs) are especially produced by microbial fermentation of dietary fibres in the intestine.

In particular, butyrate has been shown to provide various health benefits and especially to protect against obesity, insulin resistance, diabetes, to be involved in adipogenesis, in food intake, in the prevention of non-alcoholic fatty liver disease or of cardiometabolic related conditions like development of atherosclerosis, in the prevention/treatment of inflammation, infections, allergies, in the gut maturation, the gut brain axis connection, the colonic healing especially in case of colitis and to have anti-cancer effects (Lin et al., Butyrate and Propionate Protect against Diet-Induced Obesity and Regulate Gut Hormones via Free Fatty Acid Receptor 3-Independent Mechanisms, 2012; Aguilar et al, "Butyrate impairs atherogenesis by reducing plaque inflammation and vulnerability and decreasing NFκB activation", 2015; Endo et al, "Butyrate-producing probiotics reduce nonalcoholic fatty liver disease progression in rats: new insight into the probiotics for the gut-liver axis", 2013; Goverse et al, Diet-derived short chain fatty acids stimulate intestinal epithelial cells to induce mucosal tolerogenic dendritic cells, 2017; Canani et al, Potential beneficial effects of butyrate in intestinal and extraintestinal diseases, 2011; Nylund et al, Severity of atopic disease inversely correlates with intestinal microbiota diversity and butyrate-producing bacteria, 2015; Stilling et al, The neuropharmacology of butyrate: The bread and butter of the microbiota-gut-brain axis?, 2016).

Increasing butyrate production in the digestive tract is therefore in itself a therapeutic solution. It is an attractive target that provides positive health advantages (by preventing/treating some health disorders and/or by promoting some health benefits). However, orally administered SCFA are unpalatable. Some alternative solutions should therefore be developed, in particular "natural" solutions, e.g. with ingredients found in breast milk, would therefore be preferred for an administration to infants or young children.

There is clearly a need for developing suitable methods to increase the production of butyrate in the digestive tract in infants and young children.

There is also a need to deliver butyrate associated health benefits in a manner that is particularly suitable for the young subjects (infants and young children), in a manner that does not involve a classical pharmaceutical intervention as the infants or young children are particularly fragile.

There is a need to deliver such health benefits in the infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

SUMMARY OF THE INVENTION

The present inventors believe that a composition comprising at least three human milk oligosaccharides is particularly efficient to increase butyrate production in the digestive tract. They have especially demonstrated in in vitro models that the butyrate production is increased with the diversity (or complexity or number of type) of human milk oligosaccharides (more complex the mix of HMOs will be and more butyrate will be produced). In particular, the butyrate production was significantly increased with a mix of six human milk oligosaccharides (2'FL, DFL, LNnT, LNT, 3SL and 6SL) in comparison with the butyrate production obtained with one (e.g. 2'FL) or two (e.g. 2'FL and LNnT) human milk oligosaccharides tested in the same total amounts.

As previously mentioned, increasing butyrate production is in itself associated with positive health advantages. A nutritional composition comprising at least three human milk oligosaccharides (e.g. 6 HMOs) can be used to prevent and/or treat a health disorder, and/or to promote a health benefit in an infant or young child, especially a disorder or benefit influenced by/linked to the butyrate production.

In a particular embodiment, the nutritional composition according to the present invention does not comprise an oligosaccharide mixture comprising at least one N-acetylated oligosaccharide, at least one galacto-oligosaccharide and at least one sialylated oligosaccharide.

In a particularly advantageous embodiment, the nutritional composition according to the invention comprises 6 (or at least 6) HMOs that are 2'FL, DFL, LNnT, LNT, 3SL and 6SL.

DETAILED DESCRIPTION OF THE INVENTION

As used herein, the following terms have the following meanings.

The term "infant" means a child under the age of 12 months.

The expression "young child" means a child aged between one and three years, also called toddler.

The expression "child" means a child between three and seven years of age.

An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 36 weeks of gestation.

The expression "nutritional composition" means a composition which nourishes a subject. This nutritional composition is usually to be taken orally or intravenously. It may include a lipid or fat source, a carbohydrate source and/or a protein source. In a particular embodiment the nutritional composition is a ready-to-drink composition such as a ready-to-drink formula.

In a particular embodiment the composition of the present invention is a hypoallergenic nutritional composition. The expression "hypoallergenic nutritional composition" means a nutritional composition which is unlikely to cause allergic reactions.

In a particular embodiment the nutritional composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic nutritional composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The expression "growing-up milk" (or GUM) refers to a milk-base drink generally with added vitamins and minerals, that are intended for young children or children.

The term "fortifier" refers to liquid or solid nutritional compositions suitable for mixing with breast milk or infant formula.

The expression "weaning period" means the period during which the mother's milk is substituted by other food in the diet of an infant or young child.

The expression "later in life" and "in later life" can be used interchangeably. They refer to effects measured in the individual (infant or young child) after the age of some weeks, some months or some years after birth, such as after the age of 6 months after birth, such as after the age of 8 months after birth, such as after the age of 10 months after birth, such as after the age of 1 year after birth, such as after the age of 2 years, preferably after the age of 4 years, more preferably after the age of 5 years, even more preferably after the age of 7 years after birth, or even more, and as a comparison to average observations for subjects of the same age. Preferably it refers to an effect observed after at least 1 year of life, or after at least 2, 5, 7, 10 or 15 years of life. So the expression "later in life" might refer to an observation during infancy, during childhood, during the adolescent period, or during adulthood. Preferably it refers to an observation during childhood, during the adolescent period, or during adulthood.

The expression "health disorder(s)" encompass any health conditions and/or diseases and/or dysfunctions that affect the organism of an individual, including the metabolic ones.

"Body mass index" or "BMI" is defined as the value resulting from division of a numerator that is the weight in kilograms by a denominator that is the height in meters, squared. Alternatively, the BMI can be calculated from the weight in pounds as the numerator and the height in inches, squared, as the denominator, with the resultant quotient multiplied by 703. "Overweight" is defined for a human as a BMI between 25 and 30. "Obese" is defined for a human as a BMI greater than 30.

The term "SCFA" means short chain fatty acid(s).

The expression "to increase butyrate production in the digestive tract" means that the amount of butyrate, when measured in the individual in the digestive tract i.e. from the mouth to the rectum (and especially in the intestine, such as in the colon or large intestine or in a part thereof such as the caecum), is higher in an individual fed with the nutritional composition according to the present invention (i.e. comprising at least 3 HMOs) in comparison with a standard composition (i.e. a nutritional composition not comprising at least 3 HMOs, but for example comprising 0, 1 or 2 HMOs). The butyrate production in the digestive tract may be measured by techniques known by the skilled person such as by Gas-Liquid Chromatography.

The "mother's milk" should be understood as the breast milk or the colostrum of the mother.

The term "HMO" or "HMOs" refers to human milk oligosaccharide(s). These carbohydrates are resistant to enzymatic hydrolysis by digestive enzymes (e.g pancreatic and/or brush border), indicating that they may display functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide). Some examples of HMOs are the fucosylated oligosaccharides, the N-acetylated oligosaccharides and/or the sialylated oligosaccharides.

A "fucosylated oligosaccharide" is an oligosaccharide having a fucose residue. It has a neutral nature. Some examples are 2'-FL (2'-fucosyllactose or 2-fucosyllactose or 2FL or 2-FL), 3-FL (3-fucosyllactose), difucosyllactose (DFL or DiFL), lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N-neotetraose) or any combination thereof. Other examples are lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

The expression "at least one fucosylated oligosaccharide", "at least one N-acetylated oligosaccharide" and "at least one sialylated oligosaccharide" means "at least one type of fucosylated oligosaccharide", "at least one type of N-acetylated oligosaccharide" and "at least one type of sialylated oligosaccharide".

The expression "at least two fucosylated oligosaccharides", "at least two N-acetylated oligosaccharides" and "at least two sialylated oligosaccharides" means "at least two (different) types of fucosylated oligosaccharides", "at least two (different) types of N-acetylated oligosaccharides" and "at least two (different) types of sialylated oligosaccharides".

The expressions "wherein the nutritional composition does not comprise an oligosaccharide mixture comprising at least one N-acetylated oligosaccharide, at least one galacto-oligosaccharide and at least one sialylated oligosaccharide" and "wherein the nutritional composition does not comprise at least one N-acetylated oligosaccharide, at least one galacto-oligosaccharide and at least one sialylated oligosaccharide" can be used interchangeably. In some embodiments, it encompasses the expression "wherein the nutritional composition does not comprise an oligosaccharide mixture consisting of one N-acetylated oligosaccharide, one galacto-oligosaccharide and one sialylated oligosaccharide".

A "precursor of HMO" is a key compound that intervenes in the manufacture of HMO, such as sialic acid and/or fucose.

The expressions "galacto-oligosaccharide", "galactooligosaccharide" and "GOS" can be used interchangeably. They refer to an oligosaccharide comprising two or more galactose molecules which has no charge and no N-acetyl residue (i.e. they are neutral oligosaccharide). In a particular embodiment, said two or more galactose molecules are linked by a β-1,2, β-1,3, β-1,4 or β-1,6 linkage. In another embodiment, "galacto-oligosaccharide" and "GOS" also include oligosaccharides comprising one galactose molecule and one glucose molecule (i.e. disaccharides) which are linked by a β-1,2, β-1,3 or β-1,6 linkage.

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or follow-on/follow-up formula or infant cereal product or any other formulation designed for infant nutrition).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. *"Probiotics: how should they be defined"* Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

The present invention therefore refers to a nutritional composition comprising at least three human milk oligosaccharides, for use to increase butyrate production in the digestive tract in an infant or a young child.

In a particular embodiment, the nutritional composition does not comprise an oligosaccharide mixture comprising at least one N-acetylated oligosaccharide, at least one galacto-oligosaccharide and at least one sialylated oligosaccharide.

In a particular embodiment, it does not comprise an oligosaccharide mixture comprising at least one N-acetylated oligosaccharide, at least one galacto-oligosaccharide, at least one sialylated oligosaccharide and at least one fucosylated oligosaccharide.

In a particular embodiment, the nutritional composition according to the present invention does not comprise an oligosaccharide mixture consisting of one N-acetylated oligosaccharide, one galacto-oligosaccharide and one sialylated oligosaccharide.

In a particular embodiment, it does not comprise an oligosaccharide mixture consisting of one N-acetylated oligosaccharide, one galacto-oligosaccharide, one sialylated oligosaccharide and one fucosylated oligosaccharide.

In a particular embodiment, the nutritional composition according to the present invention does not contain any galacto-oligosaccharide (GOS).

In a particular embodiment, the human milk oligosaccharides are selected from the list consisting of fucosylated oligosaccharides, N-acetylated oligosaccharides, sialylated oligosaccharides and mixtures thereof.

In a particular embodiment, the nutritional composition comprises at least one human milk oligosaccharide that is a fucosylated oligosaccharide.

In a particular embodiment, the nutritional composition comprises at least one human milk oligosaccharide that is a N-acetylated oligosaccharide.

In a particular embodiment, the nutritional composition comprises at least one human milk oligosaccharide that is a sialylated oligosaccharide.

In a particular embodiment, the nutritional composition comprises at least one human milk oligosaccharide that is a fucosylated oligosaccharide and at least one human milk oligosaccharide that is a N-acetylated oligosaccharide.

In a particular embodiment, the nutritional composition comprises at least one human milk oligosaccharide that is a fucosylated oligosaccharide and at least one human milk oligosaccharide that is a sialylated oligosaccharide.

In a particular embodiment, the nutritional composition comprises at least one human milk oligosaccharide that is a sialylated oligosaccharide and at least one human milk oligosaccharide that is a N-acetylated oligosaccharide.

In a particularly advantageous embodiment, the mix of at least three human milk oligosaccharides comprises at least one fucosylated oligosaccharide, at least one N-acetylated oligosaccharide and at least one sialylated oligosaccharide.

Indeed without being bound by theory, the inventors of the present invention believe that it is particularly interesting to have at least one type of these 3 categories of HMOs and it allows getting a high butyrate production in the digestive tract (and the associated health benefits) due to a synergy between these HMOs.

In a particular embodiment, the nutritional composition comprises at least two human milk oligosaccharides that are fucosylated oligosaccharides.

In a particular embodiment, the nutritional composition comprises at least two human milk oligosaccharide that are N-acetylated oligosaccharides.

In a particular embodiment, the nutritional composition comprises at least two human milk oligosaccharides that are sialylated oligosaccharides.

In a particular embodiment, the nutritional composition comprises at least two human milk oligosaccharides that are fucosylated oligosaccharides and at least two human milk oligosaccharides that are N-acetylated oligosaccharides.

In a particular embodiment, the nutritional composition comprises at least two human milk oligosaccharides that are fucosylated oligosaccharides and at least two human milk oligosaccharides that are sialylated oligosaccharides.

In a particular embodiment, the nutritional composition comprises at least two human milk oligosaccharides that are sialylated oligosaccharides and at least two human milk oligosaccharides that are N-acetylated oligosaccharides.

The nutritional composition according to the present invention can also comprise (at least) four, five, six or even more human milk oligosaccharides.

In a particularly advantageous embodiment, it comprises six human milk oligosaccharides.

In a particularly advantageous embodiment, the nutritional composition comprises two or at least two fucosylated oligosaccharides, two or at least two N-acetylated oligosaccharides and two or at least two sialylated oligosaccharides. It is particularly interesting to have two or at least two types of these 3 categories of HMOs and it allows getting a high butyrate production in the digestive tract (and the associated health benefits) due to a synergy between these HMOs, as illustrated in examples 2 and 3.

As previously mentioned, the nutritional composition of the present invention can comprise at least one fucosylated oligosaccharide. There can be one or several types of fucosylated oligosaccharide(s). The fucosylated oligosaccharide(s) can indeed be selected from the list consisting of 2'-fucosyllactose, 3'fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list consisting of 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

In a preferred embodiment, the nutritional composition according to the invention comprises 2'-fucosyllactose (or 2FL, or 2'FL, or 2-FL or 2'-FL) and/or difucosyllactose (DFL or DiFL). It may advantageously comprise both 2'FL and DFL. In a particular embodiment, there is no other type of fucosylated oligosaccharides than a combination of 2'-fucosyllactose and difucosyllactose, i.e. the nutritional composition of the invention comprises only 2'-fucosyllactose and difucosyllactose as fucosylated oligosaccharides.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

The nutritional composition of the present invention can also comprise at least one N-acetylated oligosaccharide. There can be one or several types of N-acetylated oligosaccharide. The N-acetylated oligosaccharide(s) can be for example lacto-N-tetraose (LNT), lacto-N-neotetraose (LNnT) or any combination thereof. In some particular embodiments the N-acetylated oligosaccharide is lacto-N-neotetraose (LNnT), para-lacto-N-neohexaose (para-LNnH) or any combination thereof. In some particular embodiments the N-acetylated oligosaccharide is LNnT. In some particular embodiments the N-acetylated oligosaccharide is LNT.

In an advantageous embodiment the N-acetylated oligosaccharide is a mixture of LNT and LNnT. In some particular embodiments the composition comprises both LNT and LNnT in a ratio LNT:LNnT between 7:1 to 1:2, or between 5:1 and 1:2, or from 2:1 to 1:1, or from 2:1.2 to 2:1.6. In a particular embodiment the LNT:LNnT ratio is 5:1.

In a particular embodiment, there is no other type of N-acetylated oligosaccharides than a combination of lacto-N-neotetraose (LNnT) and lacto-N-tetraose (LNT), i.e. the nutritional composition of the invention comprises only lacto-N-neotetraose (LNnT) and lacto-N-tetraose (LNT) as N-acetylated oligosaccharides.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety. The N-acetylated oligosaccharide(s) may also be produced by biotechnological means based on microbial fermentation technology.

The nutritional composition of the present invention can also comprise at least one sialylated oligosaccharide. There can be one or several sialylated oligosaccharide(s).

The sialylated oligosaccharide(s) can be selected from the group consisting of 3' sialyllactose (3SL), 6' sialyllactose (6SL), and any combination thereof. In an advantageous embodiment the nutritional composition comprises 3SL and 6SL. In some particular embodiments the ratio between 3'-sialyllactose (3SL) and 6'-sialyllactose (6SL) can be in the range between 5:1 and 1:10, or from 3:1 and 1:1, or from 1:1 to 1:10.

In a particular embodiment, there is no other type of sialylated oligosaccharides than a combination of 3' sialyllactose (3SL), 6' sialyllactose (6SL), i.e. the nutritional composition of the invention comprises only 3' sialyllactose (3SL) and 6' sialyllactose (6SL) as sialylated oligosaccharides.

The sialylated oligosaccharide(s) may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In some aspects of the invention the at least three human milk oligosaccharides of the nutritional composition of the present invention are selected from the list consisting of 2'FL, DFL, LNnT, LNT, 3SL and 6SL.

In a particularly advantageous embodiment, the nutritional composition according to the present invention comprises six or at least six human milk oligosaccharides that are 2'FL, DFL, LNnT, LNT, 3SL and 6SL.

The present inventors have surprisingly discovered in their in vitro models that the butyrate production was increased with the diversity (or complexity or number of type) of human milk oligosaccharides (comparison was made with HMOs in the same total quantity) i.e. the more there are types of human milk oligosaccharides in the HMOs mix, the higher the butyrate production is (in other words, more complex the mix of HMOs is and more butyrate is produced). Without wishing to be bound by theory, the present inventors believe that the HMOs are acting synergically.

Therefore in an embodiment, the butyrate production is increased with the diversity (or complexity or number) of human milk oligosaccharides present in the nutritional composition according to the present invention.

The at least three human milk oligosaccharides present into the nutritional composition of the present invention may be in a total amount of from 0.1 to 10 wt %, or from 0.5 to 7 wt %, or from 0.6 to 1.5 wt % such as from 0.8 to 1.2 wt % of the nutritional composition before reconstitution with water. For reconstituted ready-to-drink formula, the total amount could be from 0.01 to 1%, more preferably 0.05 to 0.7% or 0.1 to 0.5%.

The nutritional composition according to the present invention may also comprise at least another oligosaccharide(s) and/or at least a fiber(s) and/or at least a precursor(s) of human milk oligosaccharide(s). The other oligosaccharide and/or fiber and/or precursor may be selected from the list comprising galacto-oligosaccharides (GOS), fructo-oligosaccharides (FOS), inulin, xylooligosaccharides (XOS), polydextrose, sialic acid, acacia gum, fucose and any combination thereof. They may be in an amount between 0 and 10% by weight of composition.

Suitable commercial products that can be used in addition to the oligosaccharides comprised in the oligosaccharide mixture to prepare the nutritional compositions according to the invention include combinations of FOS with inulin such as the product sold by BENEO under the trademark Orafti, or polydextrose sold by Tate & Lyle under the trademark STA-LITE®.

The composition according to the present invention may optionally also comprise at least one precursor of human milk oligosaccharide. There can be one or several precursor(s). For example the precursor of human milk oligosaccharide is sialic acid, fucose or a mixture thereof. In some particular embodiments the composition comprises sialic acid. In particular examples the composition comprises from 0 to 3 g/L of precursor(s) of human milk oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of human milk oligosaccharide.

The composition according to the invention can contain from 0 to 2.1 g of precursor(s) of human milk oligosaccharide per 100 g of composition on a dry weight basis, e.g. from 0 to 1.5 g or from 0 to 0.8 g or from 0 to 0.15 g of precursor(s) of human milk oligosaccharide per 100 g of composition on a dry weight basis.

The nutritional composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly *Bifidobacteria* and/or *Lactobacilli*.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM I-2116, *Lactobacillus johnsonii* CNCM I-1225, *Streptococcus salivarius* DSM 13084 sold by BLIS Technologies Limited of New Zealand under the designation KI2, *Bifidobacterium lactis* CNCM I-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition of the invention can further comprise at least one phage (bacteriophage) or a mixture of phages, preferably directed against pathogenic Streptococci, Haemophilus, Moraxella and Staphylococci.

The nutritional composition according to the invention is preferably a synthetic nutritional composition.

The nutritional composition according to the invention can be for example an infant formula, a starter infant formula, a follow-on or follow-up formula, a baby food, an infant cereal composition, a fortifier such as a human milk fortifier, or a supplement. In some particular embodiments, the nutritional composition of the invention is an infant formula, a fortifier or a supplement that may be intended for the first 4 or 6 months of age. In a preferred embodiment the nutritional composition of the invention is an infant formula.

The present invention also covers a growing-up milk comprising at least three human milk oligosaccharides as defined in the present invention, for use to increase butyrate production in the digestive tract in a young child or in a child.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses.

The nutritional composition of the present invention can be in solid (e.g. powder), liquid or gelatinous form.

The nutritional composition according to the invention generally contains a protein source. The protein can be in an amount of from 1.5 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, such as 1.5-1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90. In a particular embodiment a part or all the proteins are amino acids.

In a particular embodiment the nutritional composition according to the invention is a hypoallergenic composition. In another particular embodiment the composition according to the invention is a hypoallergenic nutritional composition.

The nutritional composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s).

The nutritional composition according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The human milk oligosaccharides may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The human milk oligosaccharides may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement.

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in infants or young children. The infants or young children may be born term or preterm. In a particular embodiment the nutritional composition of the invention is for use in infants or young children that were born preterm. Preterm infants may be at increased risk of metabolic diseases later in life; they may have lower immunity defences and be prone to have inflammation issues (colitis . . . ) because of the immaturity of their gut flora; they may face to problems of gut maturation . . . . So in a particular embodiment the nutritional composition of the invention is for use in preterm infants.

The nutritional composition of the present invention may also be used in an infant or a young child that was born by C-section or that was vaginally delivered.

In a particular embodiment the nutritional composition of the invention is for use in infants or young children born by C-section. These infants or young children may have lower immunity defences and be prone to have inflammation issues (colitis . . . ) because they do not encounter the vaginal mother's microbiota at birth.

In a particular embodiment the nutritional composition of the invention is for use in infants or young children at risk of developing allergies. This may be especially the case for infants or young children born from parents already suffering of allergies.

In some embodiments the nutritional composition according to the invention can be for use before and/or during the weaning period.

The nutritional composition can be administered (or given or fed) at an age and for a period that depends on the possibilities and needs.

When the nutritional composition is used for prevention purposes, it can for example be given immediately after birth of the infants. The nutritional composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4 or 6 months of birth of said infant.

In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on formula.

The present inventors have found that a specific HMOs intervention in in vitro models significantly increased the butyrate production. They have especially demonstrated that the butyrate production is increased with the diversity (or complexity or number of type) of human milk oligosaccharides. In particular, the butyrate production was significantly increased with a mix of six human milk oligosaccharides (2'FL, DFL, LNnT, LNT, 3SL and 6SL) in comparison with the butyrate production obtained with one (e.g. 2'FL) or two (e.g. 2'FL and LNnT) human milk oligosaccharides in the same total amounts, see examples 2 and 3.

As previously mentioned, increasing butyrate production is in itself associated with positive health advantages. Therefore a nutritional composition comprising at least three human milk oligosaccharides (e.g. 6 HMOs) can be used to prevent and/or treat a health disorder, and/or to promote a health benefit in an infant or young child, especially a disorder or benefit influenced by or linked to the butyrate production in the digestive tract, especially the intestinal butyrate production.

Therefore in a particular embodiment, the nutritional composition according to the present invention is used to prevent and/or treat a health disorder, and/or to promote a health benefit in an infant or a young child.

In a specific embodiment, it is used to prevent and/or treat a health disorder, and/or to promote a health benefit in an infant or a young child, wherein said health disorder or health benefit is associated with butyrate production in the digestive tract, especially the intestinal butyrate production, especially the colonic butyrate production.

The health disorder may be for example inflammation, infections, allergies, metabolic health disorders such as obesity later in life, type 2 diabetes, insulin resistance.

The health benefit may be for example gut maturation, gut brain axis connection, colonic healing especially in case of colitis, anti-cancer effects (especially against the colorectal cancer).

The health advantages targeted in the present invention may be obtained by increasing butyrate production in the digestive tract in the infant or young child, especially the intestinal butyrate production, such as the colonic butyrate production or the butyrate production in the caecum. In a particular embodiment the butyrate production in the digestive tract is measured by Gas-Liquid Chromatography and it can be expressed in nmol/mg dry weight.

In a particular embodiment, with a nutritional composition comprising the at least 3 HMOs the butyrate production in the digestive tract is increased by at least 20%, or at least 25% or at least 50% or at least 100% or at least 150% or at least 200% or at least 250% in comparison to the butyrate production in the digestive tract obtained with a nutritional composition comprising only one human milk oligosaccharide.

In another particular embodiment, with a nutritional composition comprising the at least 3 HMOs the butyrate production in the digestive tract is increased by at least at least 20%, or at least 25% or at least 50% or at least 100% or at least 150% or at least 180% in comparison to the butyrate production in the digestive tract obtained with a nutritional composition comprising only two human milk oligosaccharides.

Another object of the present invention is a growing-up milk comprising at least three human milk oligosaccharides, for use to increase butyrate production in the digestive tract (especially the intestinal butyrate production, such as the colonic butyrate production or the butyrate production in the caecum) in a young child or in a child. In a particular embodiment the growing-up milk does not comprise an oligosaccharide mixture comprising at least one N-acetylated oligosaccharide, at least one galacto-oligosaccharide and at least one sialylated oligosaccharide.

The different embodiments, details and examples previously described in the specification (e.g. related to the types and amounts of human milk oligosaccharide . . . ) also apply to this other object of the invention.

Another object of the present invention is a nutritional composition comprising at least three human milk oligosaccharides, for use to prevent and/or treat a health disorder and/or to promote a health benefit by increasing the butyrate production in the digestive tract (especially the intestinal butyrate production, such as the colonic butyrate production or the butyrate production in the caecum) in an infant or a young child. In a particular embodiment, the nutritional composition does not comprise an oligosaccharide mixture comprising at least one N-acetylated oligosaccharide, at least one galacto-oligosaccharide and at least one sialylated oligosaccharide.

This represents a new clinical situation where prevention/treatment of a health disorder and/or promotion of a health benefit can be targeted in a new way.

The different embodiments, details and examples previously described in the specification (e.g. related to the types and amounts of human milk oligosaccharide, the nutritional composition, the administration, the targeted population . . . ) also apply to this other object of the invention.

Another object of the present invention is a growing-up milk comprising at least three human milk oligosaccharides, for use to prevent and/or treat a health disorder and/or to promote a health benefit by increasing the butyrate production in the digestive tract (especially the intestinal butyrate production, such as the colonic butyrate production or the butyrate production in the caecum) in a young child or in a child. In a particular embodiment, the growing-up milk does not comprise an oligosaccharide mixture comprising at least one N-acetylated oligosaccharide, at least one galacto-oligosaccharide and at least one sialylated oligosaccharide.

This represents a new clinical situation where prevention/treatment of a health disorder and/or promotion of a health benefit can be targeted in a new way.

The different embodiments, details and examples previously described in the specification (e.g. related to the types and amounts of human milk oligosaccharide . . . ) also apply to this other object of the invention.

Another object of the present invention is the use of a nutritional composition comprising at least three human milk oligosaccharides to increase butyrate production in the digestive tract (especially the intestinal butyrate production, such as the colonic butyrate production or the butyrate production in the caecum) in an infant or a young child. In a particular embodiment, the nutritional composition does not comprise an oligosaccharide mixture comprising at least one N-acetylated oligosaccharide, at least one galacto-oligosaccharide and at least one sialylated oligosaccharide. In a particular embodiment, the use is a non-therapeutic use.

The different embodiments, details and examples previously described in the specification (e.g. related to the types and amounts of human milk oligosaccharide, the nutritional composition, the administration, the targeted population . . . ) also apply to this other object of the invention.

Another object of the present invention is the use of a growing-up milk comprising at least three human milk oligosaccharides to increase butyrate production in the digestive tract (especially the intestinal butyrate production, such as the colonic butyrate production or the butyrate production in the caecum) in a young child or in a child. In a particular embodiment, the growing-up milk does not comprise an oligosaccharide mixture comprising at least one N-acetylated oligosaccharide, at least one galacto-oligosaccharide and at least one sialylated oligosaccharide. In a particular embodiment, the use is a non-therapeutic use.

The different embodiments, details and examples previously described in the specification (e.g. related to the types and amounts of human milk oligosaccharide . . . ) also apply to this other object of the invention.

Another object of the present invention is the use of at least three human milk oligosaccharides to increase butyrate production in the digestive tract (especially the intestinal butyrate production, such as the colonic butyrate production or the butyrate production in the caecum) in an infant or a young child. In a particular embodiment, the three human milk oligosaccharides are not a combination (or does not comprise a combinaison) of one N-acetylated oligosaccharide, one galacto-oligosaccharide and one sialylated oligosaccharide.

The different embodiments, details and examples previously described in the specification (e.g. related to the types and amounts of human milk oligosaccharide, the nutritional composition, the administration, the targeted population . . . ) also apply to this other object of the invention.

Another object of the present invention is a nutritional composition comprising at least the six human milk oligosaccharides 2'FL, DFL, LNnT, LNT, 3SL and 6S, for use to prevent and/or treat a health disorder and/or to promote a health benefit in an infant or a young child, wherein the health disorder is selected from the list consisting of inflammation, allergies, metabolic health disorders such as obesity later in life, type 2 diabetes, insulin resistance, and/or wherein the health benefit is selected from the list consisting of gut maturation, gut brain axis connection, colonic healing especially in case of colitis, anti-cancer effects.

In a particular embodiment the nutritional composition does not comprise an oligosaccharide mixture comprising at least one N-acetylated oligosaccharide, at least one galacto-oligosaccharide and at least one sialylated oligosaccharide.

The different embodiments, details and examples previously described in the specification (e.g. related to the types and amounts of human milk oligosaccharide, the nutritional composition, the administration, the targeted population . . . ) also apply to this other object of the invention.

Another object of the present invention is a growing-up milk comprising at least the six human milk oligosaccharides 2'FL, DFL, LNnT, LNT, 3SL and 6S, for use to prevent and/or treat a health disorder and/or to promote a health benefit in a young child or a child, wherein the health disorder is selected from the list consisting of inflammation, allergies, metabolic health disorders such as obesity later in life, type 2 diabetes, insulin resistance, and/or wherein the health benefit is selected from the list consisting of gut maturation, gut brain axis connection, colonic healing especially in case of colitis, anti-cancer effects.

In a particular embodiment the growing-up milk does not comprise an oligosaccharide mixture comprising at least one N-acetylated oligosaccharide, at least one galacto-oligosaccharide and at least one sialylated oligosaccharide.

The different embodiments, details and examples previously described in the specification (e.g. related to the types and amounts of human milk oligosaccharide . . . ) also apply to this other object of the invention.

Other objects:

Another object of the present invention is the use of at least three human milk oligosaccharides in the preparation of a nutritional composition for increasing butyrate production in the digestive tract in an infant or a young child, wherein in a particular embodiment, the nutritional composition does not comprise an oligosaccharide mixture comprising at least one N-acetylated oligosaccharide, at least one galacto-oligosaccharide and at least one sialylated oligosaccharide.

Another object of the present invention is the use of at least three human milk oligosaccharides in the preparation of a growing-up milk for increasing butyrate production in the digestive tract in a young child or a child, wherein in a particular embodiment the growing-up milk does not comprise an oligosaccharide mixture comprising at least one N-acetylated oligosaccharide, at least one galacto-oligosaccharide and at least one sialylated oligosaccharide.

Another object of the present invention is the use of at least the six human milk oligosaccharides 2'FL, DFL, LNnT, LNT, 3SL and 6S, in the preparation of a nutritional composition for use to prevent and/or treat a health disorder and/or to promote a health benefit in an infant or a young child, wherein the health disorder is selected from the list consisting of inflammation, allergies, metabolic health disorders such as obesity later in life, type 2 diabetes, insulin resistance, and/or wherein the health benefit is selected from the list consisting of gut maturation, gut brain axis connection, colonic healing especially in case of colitis, anti-cancer effects.

Another object of the present invention is the use of at least the six human milk oligosaccharides 2'FL, DFL, LNnT, LNT, 3SL and 6S, in the preparation of a growing-up milk for use to prevent and/or treat a health disorder and/or to promote a health benefit in a young child or a child, wherein the health disorder is selected from the list consisting of inflammation, allergies, metabolic health disorders such as obesity later in life, type 2 diabetes, insulin resistance, and/or wherein the health benefit is selected from the list consisting of gut maturation, gut brain axis connection, colonic healing especially in case of colitis, anti-cancer effects.

Another object of the present invention is a pharmaceutical composition comprising at least three human milk oligosaccharides for use in increasing butyrate production in the digestive tract in an infant or a young child, wherein in a particular embodiment the pharmaceutical composition does not comprise an oligosaccharide mixture comprising at least one N-acetylated oligosaccharide, at least one galacto-oligosaccharide and at least one sialylated oligosaccharide.

Another object of the present invention refers to a method for increasing butyrate production in the digestive tract in an infant or a young child, said method comprising administering to said infant or young child a nutritional composition comprising at least three human milk oligosaccharides, wherein in a particular embodiment the nutritional composition does not comprise an oligosaccharide mixture comprising at least one N-acetylated oligosaccharide, at least one galacto-oligosaccharide and at least one sialylated oligosaccharide.

Another object of the present invention refers to a method for increasing butyrate production in the digestive tract in a young child or a child, said method comprising administering to said young child or child a growing-up milk comprising at least three human milk oligosaccharides, wherein in a particular embodiment the growing-up milk does not comprise an oligosaccharide mixture comprising at least one N-acetylated oligosaccharide, at least one galacto-oligosaccharide and at least one sialylated oligosaccharide.

Another object of the present invention refers to a method for preventing and/or treating a health disorder and/or to promote a health benefit in an infant or a young child, said method comprising administering to said infant or a young child a nutritional composition comprising at least the six human milk oligosaccharides 2'FL, DFL, LNnT, LNT, 3SL and 6S, wherein the health disorder is selected from the list consisting of inflammation, allergies, metabolic health disorders such as obesity later in life, type 2 diabetes, insulin resistance, and/or wherein the health benefit is selected from the list consisting of gut maturation, gut brain axis connection, colonic healing especially in case of colitis, anti-cancer effects.

Another object of the present invention refers to a method for preventing and/or treating a health disorder and/or to promote a health benefit in a young child or a child, said method comprising administering to said infant or a young child a growing-up milk comprising at least the six human milk oligosaccharides 2'FL, DFL, LNnT, LNT, 3SL and 6S, wherein the health disorder is selected from the list consisting of inflammation, allergies, metabolic health disorders such as obesity later in life, type 2 diabetes, insulin resistance, and/or wherein the health benefit is selected from the list consisting of gut maturation, gut brain axis connection, colonic healing especially in case of colitis, anti-cancer effects.

The different embodiments, details and examples previously described in the specification (e.g. related to the types and amounts of human milk oligosaccharide, the nutritional composition, the administration, the targeted population . . . ) also apply to all these other objects. In particular the butyrate production in the digestive tract may be the intestinal butyrate production, such as the colonic butyrate production or the butyrate production in the caecum.

EXAMPLES

The following examples illustrate some specific embodiments of the composition for use according to the present invention. The examples are given solely for the purpose of illustration and are not to be construed as limitations of the present invention, as many variations thereof are possible without departing from the spirit of the invention.

Example 1

An example of the composition of a nutritional composition (e.g. an infant formula) according to the present invention is given in the below table 1. This composition is given by way of illustration only.

TABLE 1 an example of the composition of a nutritional composition (e.g. an infant formula) according to the present invention

| Nutrients | | per 100 kcal | per litre |
|---|---|---|---|
| Energy (kcal) | | 100 | 670 |
| Protein (g) | | 1.83 | 12.3 |
| Fat (g) | | 5.3 | 35.7 |
| Linoleic acid (g) | | 0.79 | 5.3 |
| α-Linolenic acid (mg) | | 101 | 675 |
| Lactose (g) | | 10.6 | 70.7 |
| Minerals (g) | | 0.37 | 2.5 |
| Na (mg) | | 23 | 150 |
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (µg) | | 8 | 50 |
| Se (µg) | | 2 | 13 |
| Vitamin A (µg RE) | | 105 | 700 |
| Vitamin D (µg) | | 1.5 | 10 |
| Vitamin E (mg TE) | | 0.8 | 5.4 |
| Vitamin K1 (µg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (µg) | | 9 | 60 |
| Pantothenic acid (mg) | | 0.45 | 3 |
| Vitamin B12 (µg) | | 0.3 | 2 |
| Biotin (µg) | | 2.2 | 15 |
| Choline (mg) | | 10 | 67 |
| Fe (mg) | | 1.2 | 8 |
| I (µg) | | 15 | 100 |
| Cu (mg) | | 0.06 | 0.4 |
| Zn (mg) | | 0.75 | 5 |
| Oligosaccharides | 2FL (g) | 0.13 | 0.9 |
| (HMOs) | LNnT (g) | 0.0075 | 0.05 |
| | LNT (g) | 0.04 | 0.25 |
| | DFL (g) | 0.013 | 0.09 |
| | 3SL (g) | 0.014 | 0.1 |
| | 6SL (g) | 0.022 | 0.15 |

Example 2: Short-Term (Batch) Study

Description of the Study

The short-term incubation described in this section had been started simultaneously with the SHIME run (example 3). This allowed to use exactly the same faecal inoculum for both the faecal batch (Example 2) and the SHIME experiment (Example 3). An identical starting microbiota is an absolute prerequisite if the aim is to compare results obtained in both methods applied in examples 2 and 3.

At the start of the short-term colonic incubation, all test ingredients were added to sugar-depleted SHIME nutritional medium containing basal nutrients that are present in the colon (e.g. host-derived glycans such as mucin) together with a human faecal baby inoculum, partly composed of frozen and fresh faecal material. Incubations were performed during 48 h, at 37° C., under continuous mixing and anaerobic conditions. This procedure allowed to assess the specific effect of test ingredients on the metabolic and community composition profile of the colonic microbiota.

5 g/L of three different fiber blends (Mi1, Mi2 and Mi6) were tested (single dose):
Mi1: 2'FL
Mi2: 2'FL, LNnT
Mi6: 2'FL, LNnT, LNT, diFL, 3'SL, 6'SL Samples for SCFA analysis were analyzed after 0, 24 and 48 h of incubation.

Findings

Figure 1:
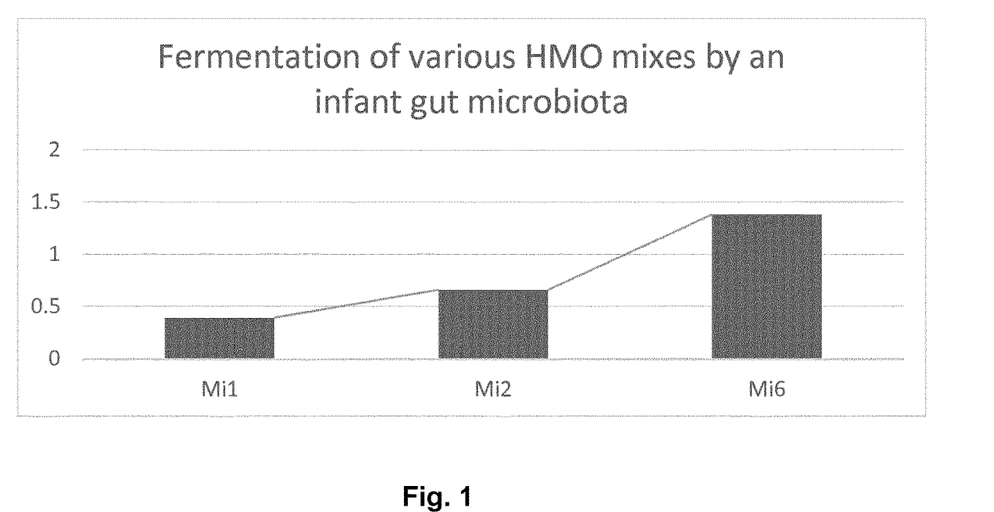
FIG. 1 represents the average butyrate production (mM) associated with the fermentation of 5 g/L of three different milk oligosaccharide blends (Mi1, Mi2 and Mi6) during the 48 h incubation (Butyrate production during short-term fermentation).
Mi1: 2'FL
Mi2: 2'FL, LNnT
Mi6: 2'FL, LNnT, LNT, diFL, 3'SL, 6'SL

FIG. 1 represents the average butyrate production (mM) associated with the fermentation of 5 g/L of three different fiber blends (Mi1, Mi2 and Mi6) during the 48 h incubation. As it can be seen, the production of butyrate was significantly increased with the HMO mix comprising 6 HMOs (Mi6: 2'FL, DFL, LNnT, LNT, 3SL and 6SL), in comparison with the butyrate production obtained with one (Mi1: 2'FL) or two (Mi2: 2'FL and LNnT) HMOs.

Its production was increased by around 250% in comparison with the production for Mi1 and by around 182% in comparison with the production for Mi2.

Example 3: Long-Term Administration Study

Description of the Study

A known continuous model of the human gastrointestinal tract was used. It is called the Simulator of the Human Intestinal Microbial Ecosystem (SHIME®). This model allows to culture the complex gut microbiota over a longer period under representative conditions for the different intestinal regions. Therefore, the SHIME® does not only allow to obtain detailed information about the fermentation profile of the prebiotic formula, but importantly also about the localization of the intestinal fermentation activity.

The first two reactors are of the fill-and-draw principle to simulate different steps in food uptake and digestion, with peristaltic pumps adding a defined amount of SHIME feed (140 mL 3×/day) and pancreatic and bile liquid (60 mL 3×/day), respectively to the stomach and small intestine compartment and emptying the respective reactors after specified intervals. The last three compartments simulate the large intestine.

The SHIME® experiment for this study consisted of three stages:

Stabilization period: After inoculation of the colon reactors with a fresh faecal sample, a two-week stabilization period allowed the microbial community to differentiate in the different reactors depending on the local environmental conditions. During this period a basic nutritional matrix was provided to the SHIME to support the optimum diversity of the gut microbiota originally present in the faecal inoculum.

Control period: During this two-week reference period, the standard SHIME nutrient matrix was further added to the model for a period of 14 days. Analysis of samples in this period allows to determine the baseline microbial community composition and activity in the different reactors, which will be used as a reference for evaluating the treatment effects.

Treatment period: During this three-week period, the SHIME reactor was operated under nominal conditions, but with a diet supplemented with the prebiotic product on top of the normal composition.

Three different fiber blends (Mi1, Mi2 and Mi6) were tested (several doses: the diet supplemented with HMOs was administered 3 times a day at a concentration of 1%):

Mi1: 2'FL
Mi2: 2'FL, LNnT
Mi6: 2'FL, LNnT, LNT, diFL, 3'SL, 6'SL

SCFA production were measured three times per week throughout the experiment.

Findings

Figure 2:
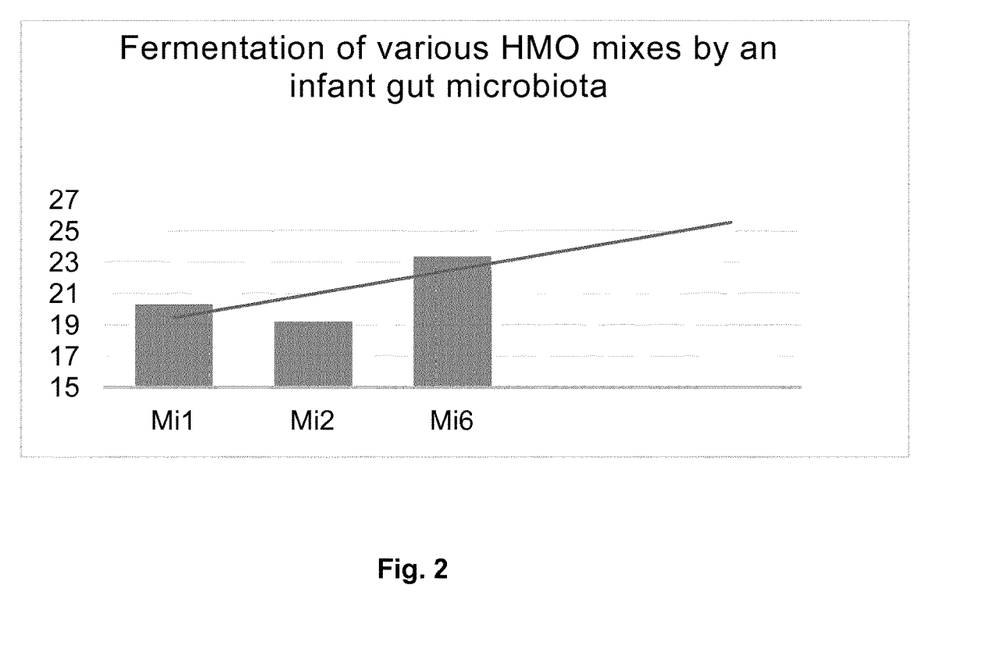
FIG. 2 represents the average of weekly butyrate production (concentration in mmol/L) after three weeks treatment with three different milk oligosaccharide blends (Mi1, Mi2 and Mi6) (Butyrate production during long-term fermentation).
Mi1: 2'FL
Mi2: 2'FL, LNnT
Mi6: 2'FL, LNnT, LNT, diFL, 3'SL, 6'SL

FIG. 2 represents the average of weekly butyrate production (concentration in mmol/L) after three weeks treatment with three different fiber blends (Mi1, Mi2 and Mi6) as previously detailed. As it can be seen, the production of butyrate was significantly increased with the HMO mix comprising 6 HMOs (Mi6: 2'FL, DFL, LNnT, LNT, 3SL and 6SL), in comparison with the butyrate production obtained with one (Mi1: 2'FL) or two (Mi2: 2'FL and LNnT) HMOs.

Its production was increased by around 28% in comparison with the production for Mi1 and by around 23% in comparison with the production for Mi2.

CONCLUSION

Whatever the model used (short term or long term), the butyrate production was increased with a HMO mix comprising at least 3 HMOs (e.g. 6 HMOs).

As previously mentioned, increasing butyrate production is in itself associated with positive health advantages. Therefore a nutritional composition comprising at least three human milk oligosaccharides (e.g. 6 HMOs) can be used to prevent and/or treat a health disorder, and/or to promote a health benefit in an infant or young child, especially a disorder or benefit influenced by/linked to the butyrate production. For example it can be used to prevent/treat inflammation, infections, allergies, metabolic health disorders such as obesity later in life, type 2 diabetes, insulin resistance. For example it can be used to promote gut maturation, gut brain axis connection, colonic healing especially in case of colitis, anti-cancer effects.

Example 4: Mouse Influenza Virus Infection Model

Mice (5 weeks old; n=30) were randomly allocated to one of the following groups: Control (n=10); 1% mixture of 2 HMOs (n=10); 1% mixture of 6 HMOs (n=10). See below table 2 for the composition of the HMO blends.

The treatments were provided in drinking water. All animals had free access to same KLIBA 2122 diet. After 2 weeks mice were challenged with Influenza strain PR8 at a dose of 100 PFU per mouse by intranasal inoculation.

Mice were monitored for the next 14 days to assess clinical score of illness symptoms and body weight loss.

Figure 3:
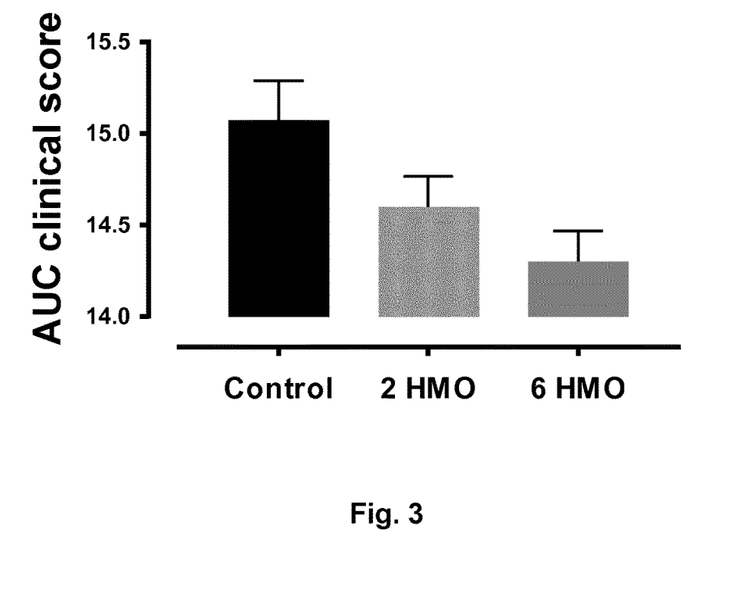
FIG. 3 represents the area under the curve of clinical symptoms of the mouse influenza virus infection model in control and 2 HMO and 6 HMO treated animals. N=10 per group, mean and SEM are shown.

The results (see FIGS. 3, 4) show that the 6 HMOs mixture provides superior protection of sickness symptoms and reduced the number of sick animals caused by the influenza virus infection compared to Control and 2 HMO treated animals. Note that the 2 HMO treatment provides intermediate protection.

TABLE 2

Composition of 2 HMO and 6 HMO mixtures as used in the mouse influenza virus infection model

|  | 2 HMO | 6 HMO |
| --- | --- | --- |
| 2'FL | 67% | 64% |
| LNnT | 33% | 5% |
| LNT | 0% | 14% |
| 3'SL | 0% | 5% |
| 6'SL | 0% | 9% |
| diFL | 0% | 5% |

The invention claimed is:

1. A method to treat a health disorder and/or to promote a health benefit in an infant or a young child in need thereof, the method comprising administering a nutritional composition to the infant or young child, the nutritional composition comprising 2'-fucosyllactose (2'FL), difucosyllactose (DFL), lacto-N-neotetraose (LNnT), lacto-N-tetraose (LNT), 3'-sialyllactose (3SL) and 6'-sialyllactose (6SL) as the only human milk oligosaccharides in the nutritional composition,
wherein the health disorder is selected from the group consisting of inflammation, allergies, and metabolic health disorders,
and/or wherein the health benefit is selected from the group consisting of gut maturation, gut brain axis connection, and colonic healing.

2. The method of claim 1, wherein the metabolic health disorders are selected from the group consisting of obesity later in life, type 2 diabetes, and insulin resistance.

3. The method of claim 1, wherein the colonic healing treats colitis in the infant or young child.

4. The method of claim 1, wherein a total amount of the 2'FL, the DFL, the LNnT, the LNT, the 3SL and the 6SL is 0.1 wt. % to 10 wt. % of the nutritional composition.

5. The method of claim 1, wherein a total amount of the 2'FL, the DFL, the LNnT, the LNT, the 3SL and the 6SL is 0.5 wt. % to 7 wt. % of the nutritional composition.

6. The method of claim 1, wherein a total amount of the 2'FL, the DFL, the LNnT, the LNT, the 3SL and the 6SL is 0.6 wt. % to 1.5 wt. % of the nutritional composition.

7. The method of claim 1, wherein a total amount of the 2'FL, the DFL, the LNnT, the LNT, the 3SL and the 6SL is 0.8 wt. % to 1.2 wt. % of the nutritional composition.

* * * * *